US00PP16666P2

(12) United States Plant Patent
Trees

(10) Patent No.: US PP16,666 P2
(45) Date of Patent: Jun. 20, 2006

(54) ***SUTERA* PLANT NAMED 'BALABLIM'**

(50) Latin Name: *Sutera hybrida*
Varietal Denomination: Balablim

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 11/017,253

(22) Filed: Dec. 20, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct *Sutera* plant named 'Balablim' characterized by its large dark lavender-colored flowers, dark green-colored foliage, good basal branching character, and spreading, trailing growth habit.

1 Drawing Sheet

Latin name of the genus and species of plant claimed: *Sutera hybrida.*
Variety denomination: 'Balablim'.

BACKGROUND OF THE INVENTION

The present invention relates to a new and distinct cultivar of *Sutera* plant botanically known as *Sutera hybrida* and hereinafter referred to by the cultivar name 'Balablim'.

The new cultivar originated in a controlled breeding program during June 2001 at Arroyo Grande, Calif. The objective of the breeding program was the development of *Sutera* cultivars with a trailing habit and large flowers.

The new cultivar was the result of the open-pollination of 'Yasflos', U.S. Plant Pat. No. 12,616. The new cultivar was discovered and selected by the inventor as a single flowering plant within the progeny of the above stated open-pollination during August 2001 at Arroyo Grande, Calif.

Asexual reproduction of the new cultivar by terminal stem cuttings since 2001 at West Chicago, Ill., has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balablim' as a new and distinct cultivar of *Sutera* plant:

1. Large dark lavender-colored flowers.
2. Dark green-colored foliage.
3. Good basal branching character.
4. Spreading and trailing growth habit.

Plants of the new cultivar differ from plants of the female parent primarily in growth habit and leaf size.

Of the *Sutera* cultivars known to the inventor, the most similar to the new cultivar is 'Bacoble', U.S. Plant Pat. No. 13,181. However, in side-by-side comparisons, conducted at West Chicago, Ill., plants of the new cultivar differed from plants of 'Bacoble' in the following characteristics:

1. Plants of the new cultivar had larger flowers than plants of 'Bacoble'.

2. Plants of the new cultivar had darker flower color than plants of 'Bacoble'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describes the colors of 'Balablim'. The plants were grown in 10 cm pots for 14 weeks in a greenhouse at West Chicago, Ill.

Figure 1:
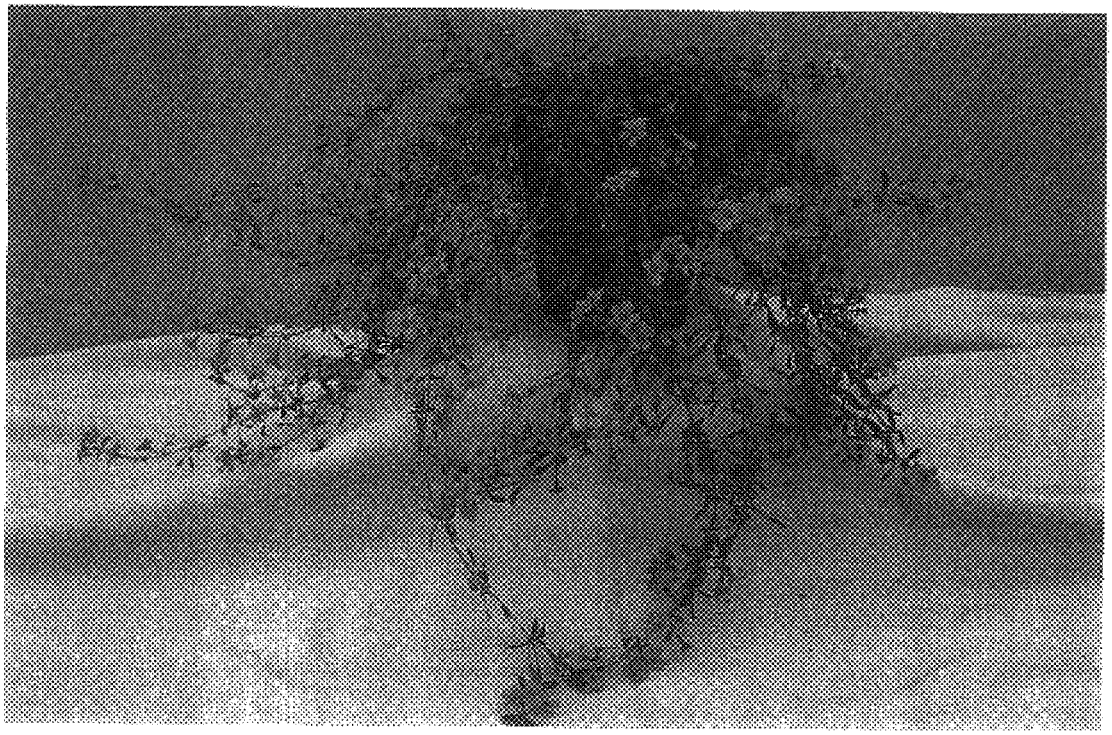
Figure 2:
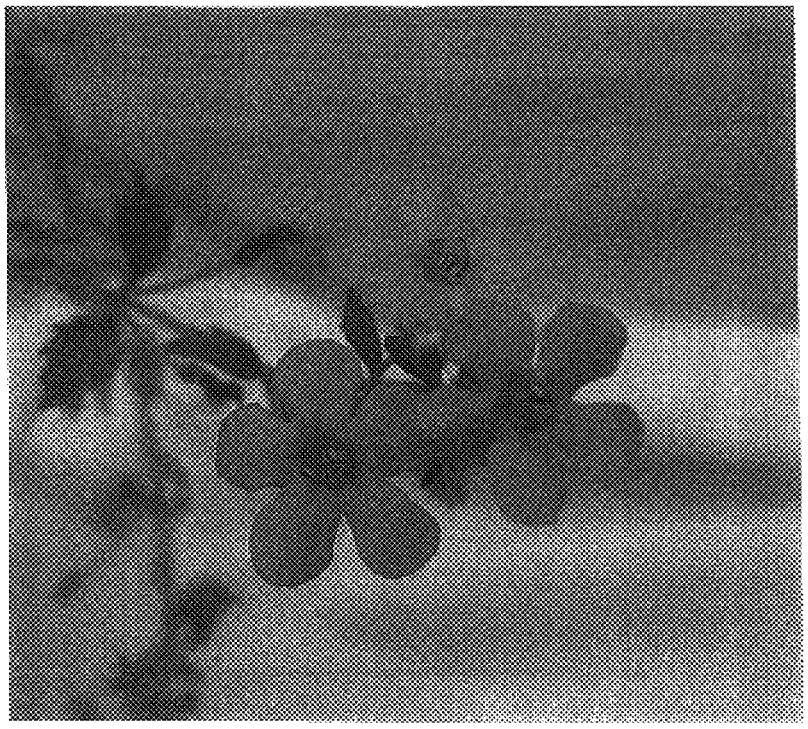

FIG. 1 illustrates a side view of the overall growth and flowering habit of 'Balablim', FIG. 2 illustrates a close-up view of an individual flower of 'Balablim'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Oct. 9, 2004, between 10:30 and 11:30 a.m. under natural light conditions.

The following descriptions and measurements describe plants produced from cuttings taken from stock plants and grown in a double polycarbonate-covered greenhouse under conditions comparable to those used in commercial practice. Plants were grown at West Chicago, Ill., in 10 cm pots for 14 weeks, using a soilless growth medium. Greenhouse temperatures were maintained at approximately 65–75° F. (18–24° C.) during the day and approximately 55–60° F. (13–15° C.) during the night. Greenhouse light levels were maintained at approximately 4,000–8,000 footcandles during the day.

Botanical classification: *Sutera hybrida*, cultivar 'Balablim'.

Parentage: Open pollination of 'Yasflos', U.S. Plant Pat. No. 12,616.

Propagation:

*Type cutting.*—Terminal stem.

*Time to initiate roots.*—Approximately 6 to 8 days.

*Time to produce a rooted cutting.*—Approximately 21 days.

*Root description.*—Fibrous.

*Rooting habit.*—Freely branching.

Plant description:

*Crop time.*—Approximately 5–7 weeks from planting of a rooted cutting.

*Growth habit.*—Moderately vigorous with good basal branching. Pinching improves basal branching.

*Form.*—Spreading and trailing.

*Size.*—Height from soil level to top of plant plane: Approximately 6.9 cm. Diameter (plant spread): Approximately 52.2 cm.

*Branch.*—Quantity: Approximately 4 main branches with lateral branches at every node. Strength: Strong, wiry. Length of main branches: Approximately 43.5 cm. Diameter of main branches: Approximately 1.5 mm. Length of lateral branches: Approximately 24 cm. Diameter of lateral branches: Approximately 0.8 mm. Texture of all branches: Densely pubescent with short soft hairs. Color of all branches: 144A with overlay at base of 187A. Internode length at middle of main branch: Approximately 2.4 cm.

*Foliage.*—Quantity: Approximately 15 leaves per main branch. Fragrance: Pungent. Form: Simple. Arrangement: Opposite. Aspect: At an obtuse angle to the stem. Shape: Elliptic. Apex: Acute. Base: Attenuate. Margin: Dentate. Venation pattern: Pinnate. Leaf length: Approximately 2.1 cm. Leaf width: Approximately 1.3 cm. Texture of upper surface: Glabrous. Texture of lower surface: Glabrous with dense pubescence along margin and veins. Color of upper surface of both young and mature foliage: Darker than 138A with venation of 145B. Color of lower surface of both young and mature foliage: 147B with venation of 145B. Petiole length: Approximately 4.0 mm. Petiole diameter: Approximately 1.6 mm. Petiole texture: Densely pubescent. Petiole color: Closest to 143C.

Flowering description:

*Flowering habit.*—Freely flowering under outdoor growing conditions with substantially continuous blooming from spring through fall, and year round in greenhouse environment.

*Time to first flower.*—Approximately 7 weeks after planting of rooted cutting.

*Lastingness of individual bloom.*—Approximately 6–9 days.

Flower description:

*Type.*—Solitary, axillary and rotate. Flowers are nonfragrant and persistent.

*Bud.*—Rate of opening: Generally takes from 3 to 4 days for buds to progress from first color to fully open flowers. Shape: Globular. Length: Approximately 7.3 mm. Diameter: Approximately 3.2 mm. Texture: Glabrous. Color: 94D.

*Corolla.*—Shape: Round. Corolla is composed of five obovate petals fused at base forming a tube. Corolla diameter: Approximately 1.6 cm. Petal appearance: Dull. Petal length from tube opening: Approximately 6.4 mm. Petal width: Approximately 5.7 mm. Petal apex: Obtuse. Petal margin: Entire. Petal texture of upper and lower surface: Glabrous. Color of upper surface of petals when flower is opening and when fully opened is closest to N87C. Color at base of petals, around tube opening, and into tube: 17B. Color of lower surface of petals both when opening and when fully opened: Closest to N87D.

*Corolla tube.*—Length: Approximately 6.7 mm. Diameter at throat: Approximately 3.5 mm. Diameter at base: Approximately 1 mm. Texture of inner surface: Densely pubescent. Texture of outer surface: Densely pubescent. Color of inner surface: 4D at base, 17B at apex. Color of outer surface: 4D at base, 15C at apex.

*Calyx.*—Formed by five sepals, fused at base to form tube. Calyx length: Approximately 5.1 mm. Calyx diameter at apex: Approximately 0.6 mm. Calyx diameter at base: Approximately 3 mm. Sepal shape: Linear. Sepal apex: Acute. Sepal margin: Entire. Sepal length: Approximately 5.1 mm. Sepal width: 0.6 mm. Texture of upper surface of sepal: Glabrous. Texture of lower surface of sepal: Densely pubescent. Color of upper and lower sepal surfaces: 143C.

*Pedicel.*—Strength: Strong. Aspect: At an acute angle to the stem. Length: Approximately 9.4 mm. Diameter: 0.6 mm. Texture: Densely pubescent. Color: 143C.

*Reproductive organs.*—Androecium: There are 4 stamens fused to the inside of the corolla tube, 2 above and 2 below the stigma. Anther shape: Funnel. Anther length: Approximately 1.2 mm. Anther color: 4D at base, 166B at apex. Pollen amount: Abundant. Pollen color. 13A. Gynoecium: Pistil quantity: One. Pistil length: Approximately 9.8 mm. Stigma length: Approximately 0.6 mm. Stigma color: Lighter than 151D. Style length: Approximately 7.3 mm. Style color. 150B. Ovary diameter: Approximately 1.9 mm. Ovary color: 143C.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera hybrida* plant named 'Balablim', substantially as herein shown and described.

* * * * *